United States Patent [19]
Flegal et al.

[11] 4,453,220
[45] Jun. 5, 1984

[54] APPARATUS AND METHODS FOR RECORDING ANTIMICROBIC SUSCEPTIBILITY DATA AND BIOTYPE DATA

[76] Inventors: Philip B. Flegal, 2416 Kathy Way, Calistoga, Calif. 94515; Michael V. Lancaster, 201 Carl Dr., Chapel Hill, N.C. 27514; William W. Hanney, III, 2425 Janis Way, Calistoga, Calif. 94515

[21] Appl. No.: 239,441

[22] Filed: Mar. 2, 1981

[51] Int. Cl.³ .................... G06F 15/20; G01N 33/16
[52] U.S. Cl. .................................... 364/413; 364/497
[58] Field of Search ............... 364/413, 496–499; 435/32, 291

[56] References Cited
U.S. PATENT DOCUMENTS

| | | | |
|---|---|---|---|
| 3,748,044 | 7/1973 | Liston | 364/497 X |
| 3,832,532 | 8/1974 | Praglin et al. | 364/413 |
| 4,236,211 | 11/1980 | Arvesen | 364/413 |
| 4,236,894 | 12/1980 | Sommervold | 364/497 X |
| 4,281,387 | 7/1981 | Kraft et al. | 364/497 |

FOREIGN PATENT DOCUMENTS 2949190 6/1981 Fed. Rep. of Germany ...... 364/413

*Primary Examiner*—Edward J. Wise
*Attorney, Agent, or Firm*—Flehr, Hohbach, Test, Albritton & Herbert

[57] ABSTRACT

A microprocessor based apparatus and method for recording antimicrobic susceptibility data and biotype data. Manual data entry means in the form of two separate arrays of switches are provided for entering susceptibility data from microdilution test panels and a biochemical identification panels. An LED array is provided in a test panel housing on the front panel of the instrument cabinet in which the system is housed for feedback of data entry under microprocessor control. A microprocessor system records the entered well coordinated data for the microdilution test panel wells and the biochemical identification panel wells and converts the entered data into a printout of the minimum inhibitory concentration (MIC) of antimicrobics in the MIC test panel and a probable identification of the unknown microorganism. A multicopy form is provided for the printout from a printer functioning under microprocessor control. The printout includes both human readable MIC and biochemical identification information and a machine readable code for subsequent entry of the information into a data base.

20 Claims, 6 Drawing Figures

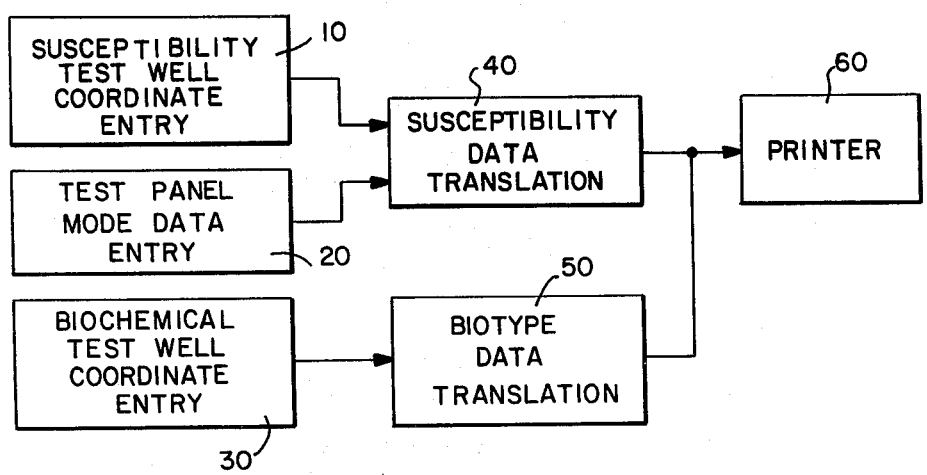
FIG.—1
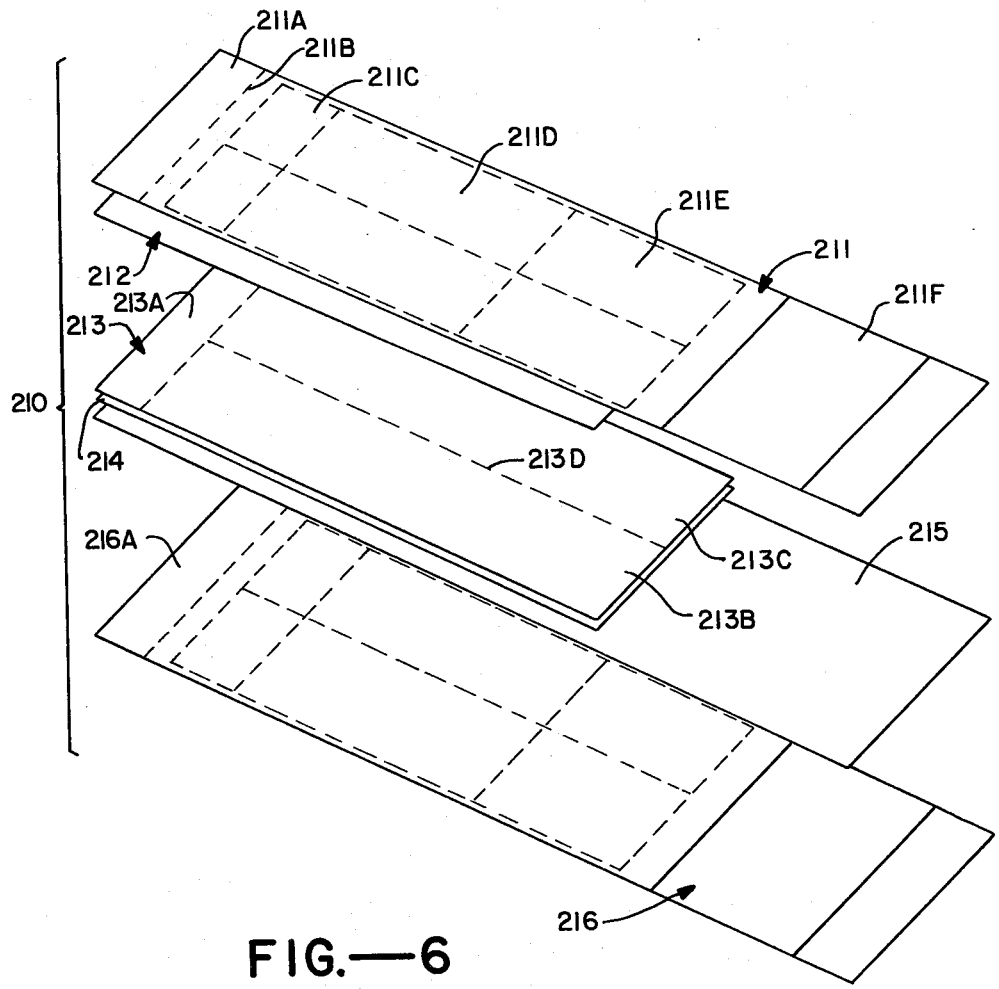
FIG.—6

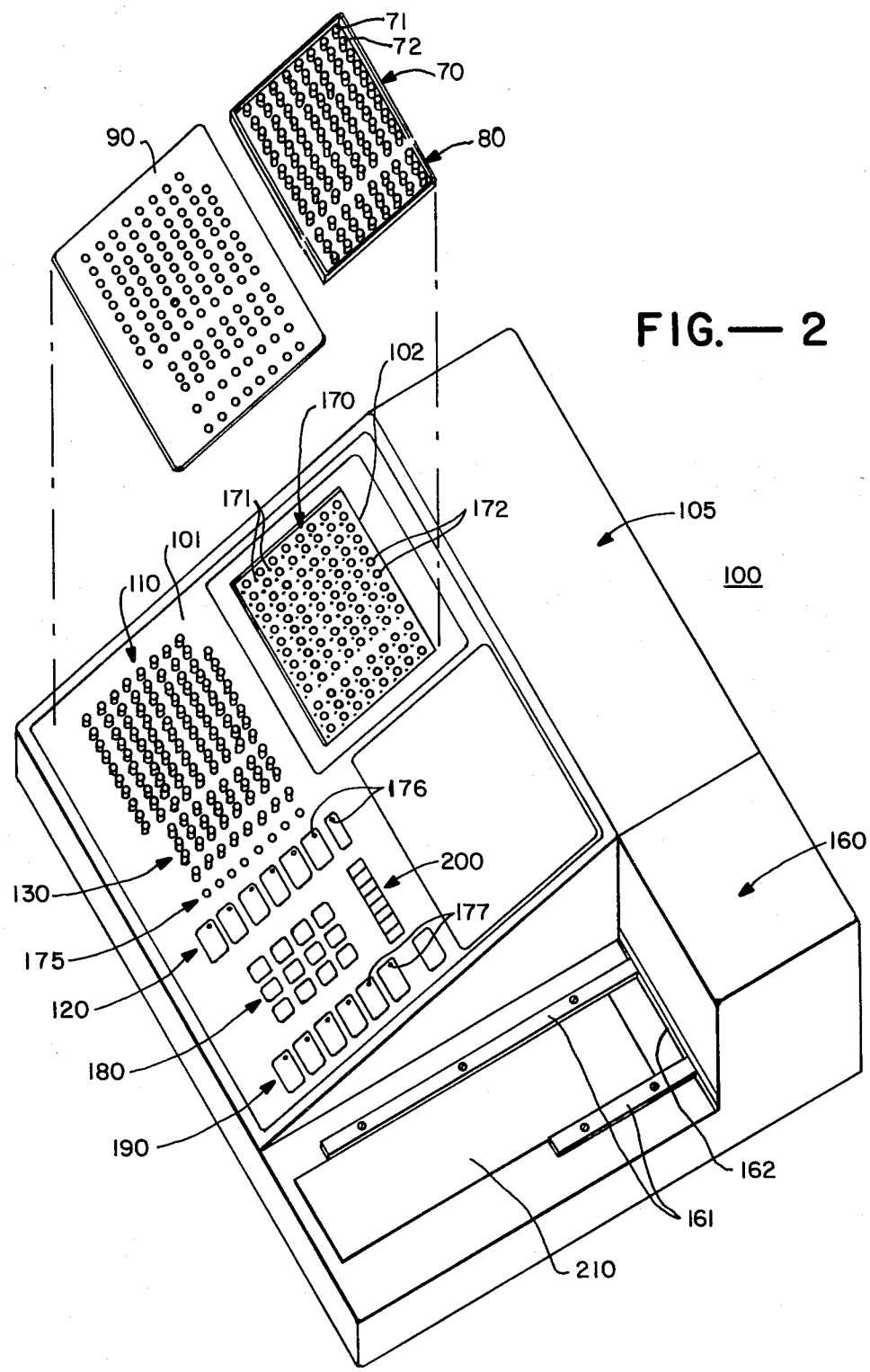
FIG.—2

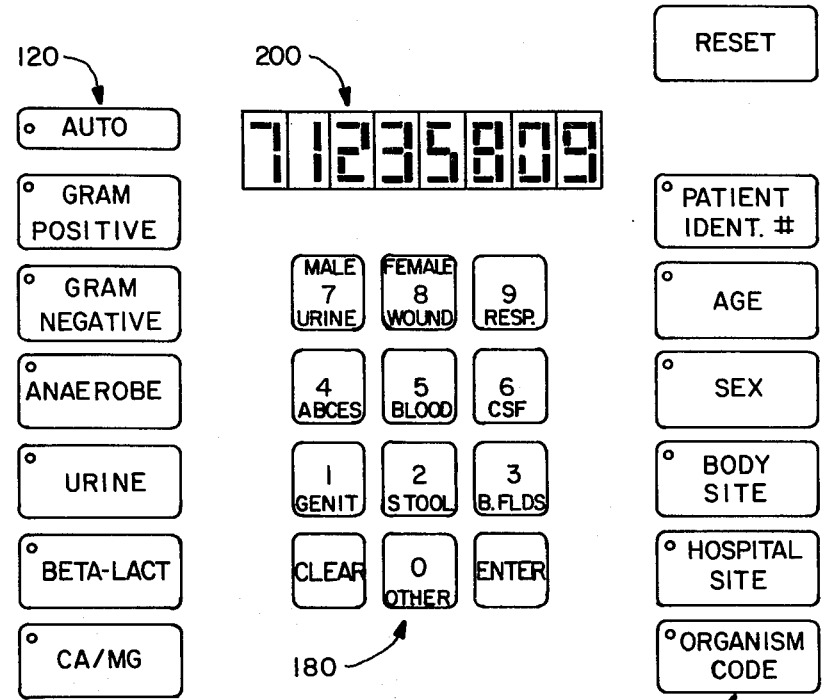

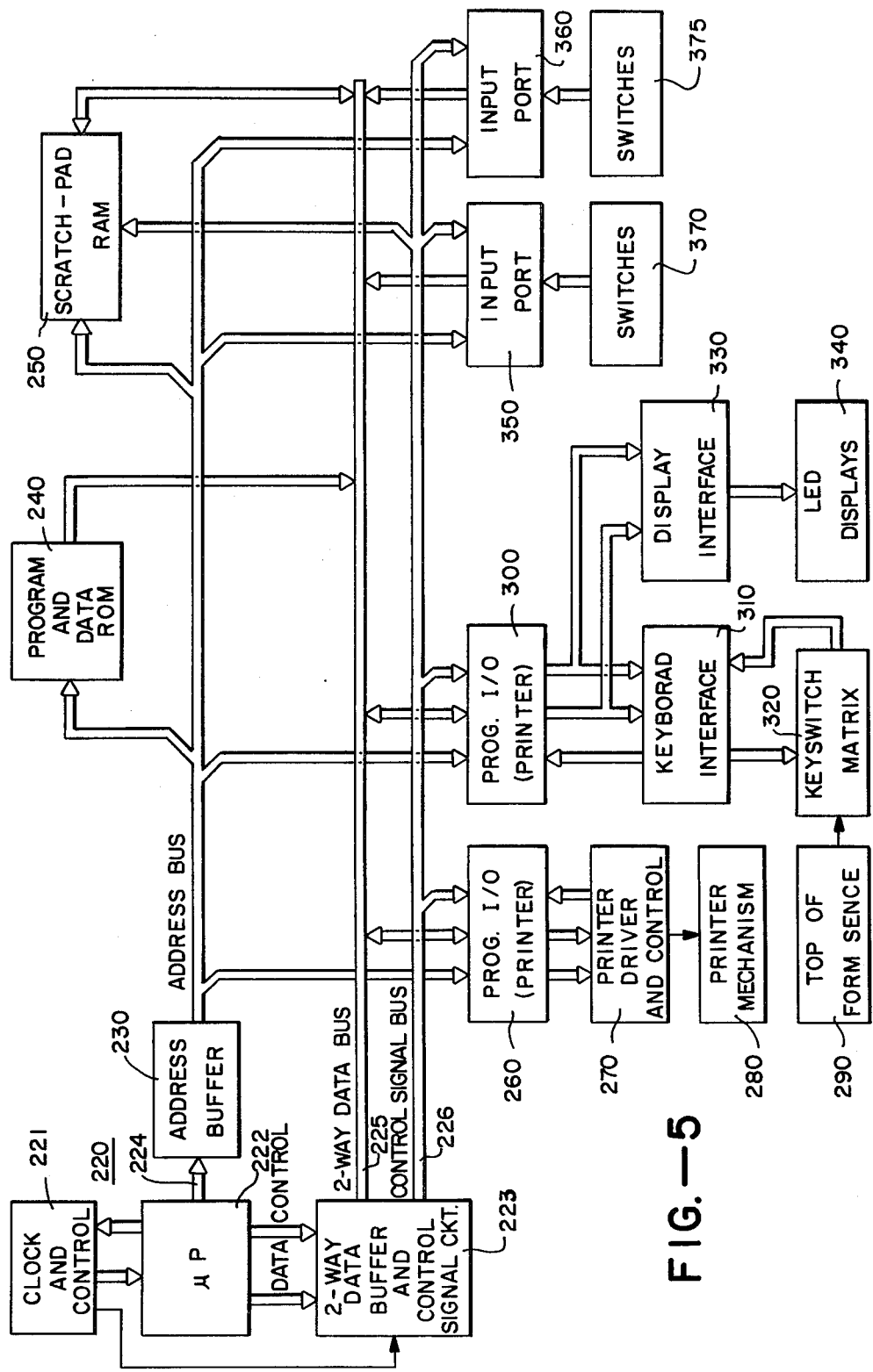
FIG.—5

APPARATUS AND METHODS FOR RECORDING ANTIMICROBIC SUSCEPTIBILITY DATA AND BIOTYPE DATA

This invention relates generally to apparatus and methods for recording data from biochemical tests and, more specifically, to apparatus and methods for recording antimicrobic susceptibility data from microdilution minimum inhibitory concentration test panels and biotype data from a biochemical test panel.

Microdilution test panels for determining the minimum inhibitory concentration (MIC) of various antimicrobics against infectious aerobic organisms have been commercially available for several years. Recently a microdilution test panel for anaerobic organisms has also become commercially available. There are two separate test panels for aerobic bacteria, one for gram positive type organisms and one for gram negative type organisms. The test panel for the anaerobic bacteria is a single type. For gram negative aerobic bacteria there is also commercially available a biochemical identification panel which provides a reliable system for identification of most clinically significant enteric and non-enteric gram negative bacteria.

For purposes of discussion of this invention the microdilution MIC test panels and gram negative identification panel available from Micro-Media Systems, Inc. of Potomac, Maryland will be utilized, although it should be understood that the invention could also be applied to susceptibility test panels and biochemical identification panels available from other commercial sources. Microdilution MIC panels utilize the classical broth tube dilution method for determining the minimum concentration of various antimicrobics which inhibit the growth in vitro of infectious organisms. MIC aerobic test panels currently available from Micro-Media Systems consist of molded plastic plates containing eighty wells in a ten by eight array. The top row of wells consist of a sterility control well and a growth control well together with a plurality of antimicrobics in single dilution at breakpoint concentrations. The remainder of the test panel consists of a ten by seven array of wells with each of the ten columns associated with a specific antimicrobic agent and each of the seven wells in each column having a different dilution of the associated antimicrobic. FIG. 3 illustrates the serial microdilution values in micrograms per milliliter for a gram negative MIC panel where the circles within the dashed rectangle represent the ten by eight array of wells and the single or multidilution concentrations in each well. The alphabetic identification over the third through sixth well in the first row designates four antimicrobics in single dilution with the shorthand antimicrobic reference being as follows: "CLST" stands for Colistin, "FDTN" represents Nitrofurantoin, "T/S" stands for Trimeth/Sulfa, and "KANA" stands for Kanamycin. The antimicrobics in the columns of the ten by seven array are designated at the bottom of the array of circles in FIG. 3 with the shorthand alphabetic designations designating from left to right the following antimicrobic agents: Ampicillin, Cephalothin, Gentamicin, Tetracycline, Carbenicillin, Chloramphenicol, Tobramycin, Amikacin, Cefamandole, Cefoxitin.

The single and multiple dilution antimicrobics which are provided in the gram positive and anaerobe panels are set forth in the literature which is supplied with each test panel. Some of the antimicrobics are common to the various test panels, but generally each test panel will contain some unique antimicrobics with different serial dilution values such that for each test panel there is a unique relationship between a particular test well coordinate and a corresponding dilution of an associated single or multiple dilution antimicrobic.

At the manufacturer's facility antimicrobic powders for a particular test panel are brought to aqueous solution and diluted in a selected broth to concentrations which bridge the range of clinical interest. Single dilutions of the single dilution antimicrobics on each panel are placed in the single dilution wells and the serial dilutions for the multiple microdilution wells are supplied to the remainder of the wells in the panel. The test panels are then quickly frozen to preserve antimicrobic effectiveness and are delivered in a frozen condition to the test laboratory. At the laboratory the panels are maintained in a frozen condition until they are to be used. The trays to be used on a particular day are then thawed and one panel of an appropriate type is utilized for each unknown organism to be tested.

The microorganism specimens to be tested may be supplied to the laboratory from a number of sources. The specimens may be collected by doctors in their various offices and sent to a central testing laboratory or the specimens may have been collected from patients in a hospital with which the laboratory is associated. The microorganism specimens may come from various parts of the patient's body, for example, from cerebral spinal fluid, an abscess, an infected wound, a genital infection, etc. The collected specimens are cultured on a primary agar plate in accordance with normal laboratory practice. From the bacterial colonies on the primary culture plate an innoculum is prepared in accordance with an established procedure which produces a bacterial suspension of a prearranged concentration. Innoculation of the test wells in the test panel is carried out by first pouring the innoculum into a seed trough supplied with the test panel. Then a disposable innoculator supplied with the test panel is inserted in the seed trough. The innoculator is then lifted from the seed trough and lowered into the MIC test panel with the prongs on the innoculator entering all wells except the sterility control well in the upper lefthand corner of the panel. The prongs on the innoculator touch the media in the test panel and a predetermined amount of the innoculum is pulled off of the prongs by capillary action so that each well in the test panel will be innoculated with a predetermined uniform concentration of the bacterial suspension. Thereafter, the innoculated panels are incubated overnight under prescribed conditions to promote microorganism growth in those wells which do not contain a sufficient growth-inhibitory concentration of the antimicrobic.

After incubation, the technologist places the test panel in a panel reader which provides an indirectly-lighted background and places a mask overlay over the panel which identifies the contents of each well. After checking that the sterility control well is clear and that there is turbidity in the growth control well, the test results in the single dilution wells are read for presence or absence of organism growth and recorded on an appropriate form. Then the minimum inhibitory concentration for each antimicrobic is manually recorded by visually inspecting the array of test wells and determining in each column the end point of microorganism growth. The lowest antimicrobic concentration which shows complete inhibition of organism growth is recorded as the minimum inhibitory concentration for that particular antimicrobic. If all of the dilutions for an antimicrobic permit growth, the end point is recorded as greater than the highest concentration provided in the panel. If all of the dilutions for a particular antimicrobic show an inhibition of growth, the end point for that antimicrobic is recorded as less than or equal to the lowest concentration tested. Generally the technologist reading the test panel will record the test results manually by writing the MIC values on both a patient report form and a laboratory log book. As is true of all manual data recording methods, the manual recording of MIC data on various forms sometimes results in transcription errors. In addition manual data recording requires significant technologist time and thus impacts the number of tests that can be performed by the technologist on any particular day.

If the particular microorganism is a gram positive or anaerobic organism, only microdilution MIC test panels are available for these types of organisms at present and no biochemical identification test will be run. Consequently, once the technologist has recorded the MIC data from the microdilution MIC panel for these microorganisms the technologist's work thereon is completed. However, the most common microorganisms are gram negative organisms and for such organisms an identification (ID) panel is also available for the technologist to utilize to identify the unknown microorganism in accordance with a standardized testing procedure. As shown in FIG. 2, the gram negative ID panel 80 consists of a three by eight array of test wells each of which is utilized for performing a particular primary biochemical test and selected ones of which are also utilized to conduct secondary on-panel tests. In addition to the on-panel primary and secondary tests, the biochemical identification scheme implemented using the biochemical ID panel may require certain off-panel tests to be conducted and data from these off-panel tests to be included in the calculation of a biotype code for the unknown microorganism. FIG. 3 illustrates within the dashed rectangle 92 the primary on-panel tests associated with each of the wells in the three by eight array and the secondary and off-panel tests which may be utilized.

The biochemical ID scheme carried out using the gram negative ID panel is complicated by the fact that gram negative microorganisms fall into two general categories, i.e. enteric and non-enteric organisms. In order for the ID scheme to permit identification of both enteric and non-enteric organisms, some portions of the biotype coding scheme for the two different types of organisms are different. The general principle involved in the biotype identification scheme is the grouping of primary and secondary on-panel tests and off-panel tests into biochemical reaction groups each involving three reactions and with each of the three reactions having a particular point value contribution to a biotype code digit. Some of the biochemical tests are common to both enteric and non-enteric microorganisms and some of the tests are specific to one or the other of these types. In other words, some of the biochemical on-panel tests are utilized to generate one of the digits of a biotype code for only enteric organisms and some are used to develop a biotype code number for only non-enteric organisms. The principal complexity in the scheme of developing biotype code digits separately for enteric and non-enteric organisms is that the indole reaction has a different point value depending on whether the organism is enteric or non-enteric and furthermore the indole reaction contributes to a different one of the biotype code digits for enteric and non-enteric organisms.

The biotype code development scheme is generally illustrated in FIG. 3. As shown, the Oxidase (Ox), Dextrose (Dx), and VP tests are common to both the enteric and non-enteric biotype identification scheme and are utilized to develop the first code digit for both types of gram negative organisms. This is indicated by the designations ED1 and $\overline{ED1}$ for the dashed line interconnecting these three test well locations. The point value for each test is indicated within the circle. In the prior art scheme of manual recording of the biochemical ID data, the positive or negative character of these three tests would be recorded on a gram negative identification worksheet which indicates the point value for each of the positive reactions noted. The technologist then adds together the point values of the positive reactions and writes a biotype code number in an appropriate code number block on the form.

Since there are off-panel tests which must be conducted for non-enteric organisms, it is important that the technologist identify at the time the test panel is set up at least whether the unknown organism is probably non-enteric. This is principally done by first performing the off-panel Oxidase test and if this test shows positive then a non-enteric organsim is suspected and the secondary on-panel test for Nitrate (Ni) reduction, and the off-panel tests which are growth on MacConkey agar (Mac) and Motility (Mot) are set up by the technologist along with the gram negative ID panel. At this point then the technologist is prepared to complete the identification tests required for non-enteric organisms.

As shown in FIG. 3, the second biotype code digit for both enteric and non-enteric organisms is developed using the same three biochemical tests: ONPG (ON), hydrogen sulphide ($H_2S$), and Lysine (Ly). The third digit of the biotype code for both enteric and non-enteric organisms is also developed using the same three biochemical tests: Arginine (Ag), Ornithine (Or), and Urea (Ur). However, the biochemical tests utilized to develop the fourth digit of the biotype code are different for enteric and non-enteric organisms. For enteric organisms the fourth digit is developed using the combination of the following three tests: Citrate (Ci), Malonate (Ma), and Tryptophane Deaminase (TDA). For the fourth digit of the non-enteric biotype code, the Citrate and Malonate reactions are used, but the Indole reaction is the third test. For enteric organisms the Indole reaction enters into the fifth digit of the biotype code along with Lactose (La) and Sucrose (Su). At this point the groups of biochemical tests which are utilized to develop the biotype code digits five, six, and seven are completely different for the enteric and non-enteric organisms. The fifth digit for enteric organisms is developed using Esculin Hydrolysis (EH), Acetamide (Ac), and OF Dextrose (OFD). The sixth and seventh biotype code digits utilize different groups of biochemical reactions as shown in FIG. 3. Once the technologist has confirmed whether the organism is enteric or non-enteric he utilizes the gram negative identification worksheet to record the positive and negative reactions which are pertinent to that particular organism and then calculates the biotype code digit from the three reaction groupings which are set forth on the form. Once the technologist has calculated the biotype identification code he can then look up the biotype code in a code book containing the biochemical identification data base and determine and record the most probable microorganism identification. If the laboratory is accumulating MIC and biotype code information using a data service bureau operated by Micro-Media Systems, Inc. then the MIC listing and biotype code are recorded along with various epidemiology data on a special form for entering into the data base through an optical character reader. The manual calculations of the biotype code numbers and the manual recording of the code number and probable microorganism identifications are all subject to possible technologist error which is cumulative with the possible transcription errors which may occur in connection with the recording of minimum inhibitory concentration data. In addition, the multiple manual recording of the susceptibility data and biotype code data occupies significant technologist time, and thus negatively impacts technologist productivity and overall patient care costs.

Accordingly, it is an object of this invention to provide apparatus and methods for recording antimicrobic susceptibility data from microdilution MIC test panels.

It is a further object of this invention to provide apparatus for automatically processing biochemical test data into a record of probable identification of the unknown microorganism tested.

It is a further object of this invention to provide apparatus and methods for recording antimicrobic susceptibility data which is capable of providing printout listings of minimum inhibitory concentration data for a plurality of MIC test panel types.

It is a further object of this invention to provide apparatus for automatically computing and printing out a biotype identification code from entered biochemical test data.

It is a further object of this invention to provide apparatus and method for producing a printout of minimum inhibitory concentration data on a special multi-copy form which eliminates manual transcription requirements.

It is a further object of this invention to provide a printout of minimum inhibitory concentration data and biotype code data on a special form in both human-readable and machine-readable fashion.

One aspect of this invention features a system for recording susceptibility data from one of a plurality of microdilution test panel types which have been described above. The system includes a first data entry means for manually entering susceptibility data in the form of the coordinates of one of the wells in each of said sets at the breakpoint of microorganism growth based on visual inspection of the wells of the test panel. A second data entry means is provided for entering test mode data corresponding to the test panel type. A printer is provided for printing alphanumeric data on a prescribed form and a susceptibility data translation means translates the entered susceptibility data in terms of the entered mode information into printer drive signals for driving the printer to print on the form a listing of minimum inhibitory concentrations of the antimicrobics in the test panel for the culture being tested. Preferably the prescribed form is a multi-sheet, duplicating data form having at least one of the sheets with a pair of peel off self-adhesive labels thereon and the susceptibility data translation means drives the printer to print a duplicate of the minimum inhibitory concentration listing on each of the peel off labels to eliminate any transcription by the technologist.

In accordance with another aspect of this invention a system is provided for not only recording susceptibility data but also being further adapted for recording biotype data from a biochemical microorganism identification panel of the type previously described. A system having this feature further includes a third data entry means for manually entering biotype data in the form of the coordinates of wells having a prearranged one of a predefined positive or negative reaction and the preassigned coordinates of secondary and separate tests having a prearranged one of a predefined positive or negative reaction. Biotype data translation means is provided for translating the entered biotype data into printer drive signals for driving the printer to print out at least one probable microorganism identification corresponding to the entered biotype data unless, of course, the biotype is determined to be invalid according to known parameters regarding known types of organisms.

In one version of the biotype data translation means a multidigit biotype code number is calculated from the biotype data entered on the third data entry means. The biotype data translation means further includes a means for storing probable microorganism identifications corresponding to each of a large number of biotype code numbers and means for retrieving the stored microorganism identifications corresponding to a calculated biotype code number and driving the printer to print out the probable microorganism identification corresponding to the calculated biotype code.

In a preferred version of the invention, a susceptibility data display means including an array of visual display elements corresponding substantially to the geometric arrangement of the sets of wells in the microdilution test panel is provided. Furthermore, a display driver means is provided for translating the entered susceptibility data into display driver signals causing the display means to display visual indicia of the entered susceptibility well coordinate data. As applied to a system in which biochemical identification data is also recorded, a second data display means is provided having an array of visual display elements corresponding substantially to the geometric arrangement of the wells in the biochemical identification panel together with a third data display means including a plurality of visual display locations assigned to secondary panel tests and off-panel biochemical tests. The display driver means translates the entered susceptibility data and the entered biochemical test data into display driver signals for causing the first display means to display visual indicia of the entered susceptibility test well coordinates, for causing the second display means to display visual indicia of entered on-panel biochemical test well coordinates and for causing the third display means to display visual indicia of entered coordinates for the secondary and off-panel tests.

In a preferred embodiment all of the data entry means are switches with the data entry means for the susceptibility data consisting of a plurality of sets of switches arranged in a geometric array corresponding substantially to the geometric arrangement of the sets of wells in the microdilution test panel for manual entry of the susceptibility coordinate data by actuation of one of the switches corresponding to an associated well location. Similarly, the data entry means for the biochemical test data comprises a plurality of sets of switches arranged in a geometric array corresponding substantially to the array of biochemical test wells in the panel together with a separate set of switches for the secondary and off-panel tests. The sets of switches are adapted for manual entry of the biochemical test data by actuation of one of the switches corresponding to an associated biochemical test panel well location or to an assigned coordinate location for a secondary or off-panel test.

In a preferred embodiment the data recording system is housed in an instrument cabinet which has a front panel which includes a test panel well adapted to receive one or both of an MIC test panel and a biochemical test panel with illumination means mounted under the front panel for illuminating test panels inserted therein. Preferably in this embodiment the data display means comprises a circuit board mounted in the test panel well and having a plurality of light elements mounted thereon in an array corresponding to the array of wells in the test panel at positions adjacent corresponding well locations in the test panel.

In a preferred embodiment of the data recording system of this invention the printer comprises a printer mechanism and a printer drive circuit adapted to respond to input data and control signals to print alphanumeric characters on a predesigned form. The preferred embodiment utilizes a microprocessor-based susceptibility data translation means. A first programmable port is coupled to the address data and control buses of the microprocessor for selectively supplying data and control signals to the printer drive circuit under microprocessor program control. A second programmable port is coupled to the first and second data entry means and to the address data and control buses of the microprocessor for enabling the microprocessor to receive susceptibility data and test mode data. A random access memory is coupled to the address data and control signal buses for storing the susceptibility data and the test mode data under microprocessor program control. A program and data memory is coupled to the address and data buses for storing microprocessor operating program codes and a plurality of minimum inhibitory concentration data images, each of the data images corresponding to all of the susceptibility test well coordinates and associated antimicrobic concentrations for a particular one of the microdilution test panel types. The microprocessor operating program codes stored in the program and data memory establish a first microprocessor operating status during which the second programmable port is active to permit entry and storage of the susceptibility and test mode data and a second microprocessor operating status during which the second programmable port is active and the microprocessor is instructed to utilize the stored susceptibility and test mode data to selectively access portions of a corresponding MIC data image in the program and data memory for communicating corresponding data and control signals to the printer to cause a printout of a listing of the minimum inhibitory concentrations of the antimicrobics for the unknown microorganism. The preferred embodiment also includes a data display means in the form of a plurality of display elements arranged in an array corresponding substantially to the geometric arrangement of the sets of wells in the microdilution test panel. Display driver means are coupled to the second programmable port for driving the display means to actuate display elements corresponding to entered susceptibility well coordinate data under microprocessor control.

In a preferred version of the system of this invention which is further directed to recording biotype identification data, the system utilizes the microprocessor as both a susceptibility data translation means and the biotype data translation means. The microprocessor program codes active during the first microprocessor operating status include microprocessor program instructions for translating each of the entered biotype data coordinates into an associated biotype code digit value, for summing the biotype code digit values with others previously entered for the same digit, and for storing the summed biotype code digit values in the random access memory. Furthermore, the microprocessor program codes which are active during the second microprocessor operating status include microprocessor program instructions for retrieving the stored biotype code digit values and communicating corresponding data signals to the printer for printing a biotype identification code number on the form.

In the preferred instrument embodiment the program and data memory also stores a data table which correlates each of a large number of the biotype identification code numbers with a corresponding list of probable microorganisms which may produce that biotype identification code. The microprocessor program codes which are active during the second operating state includes microprocessor program instructions for looking up the probable microorganism data in the data table based on the stored biotype identification code number and communicate corresponding data signals to the printer for printing out the probable microorganism identification on the form. According to the preferred version of this invention minimum inhibitory concentration data and biotype data are printed both in human-readable and machine-readable format on separate portions of the form to eliminate all requirements for manual recording of data by the technologist.

From the above description of the features of this invention, it should be apparent that the data recording system provided by this invention provides numerous advantages over the manual data recording system previously utilized by technologist working with MIC test panels and biochemical identification panels. Utilizing the system of this invention, entry of susceptibility test data can be accomplished very rapidly since all the technologist must do is locate the lowest concentration well in each column which shows an absence of microorganism growth and enter the coordinates of that well location. Once this has been accomplished for all of the microdilution test wells including both serial and single dilution wells, the system will automatically print out a listing of minimum inhibitory concentrations of the appropriate antimicrobics in accordance with the test mode data which the technologist has also entered into the system. When utilized for recording biochemical identification data, the system also permits quick entry of biochemical test data by the technologist and automatically performs the tasks which previously had to be manually carried out by the technologist to derive a biotype code number and to determine a probable microorganism identification therefrom. Accordingly, the system of this invention greatly increases the productivity of the technologist in recording susceptibility and biochemical identification data and eliminates the possible errors which may be introduced into data recording by erroneous transcription of data by the technologist miscalculation of a biotype code, or misreading of a probably microorganism identification based on the biotype code.

In addition, the preferred form of the system of this invention which incorporates a microprocessor-based system for translating entered susceptibility data and biochemical test data into appropriate MIC printouts and biotype code printouts, is extremely flexible in terms of handling changes which might be made in MIC and/or biochemical test panels. Additional types of test panels can readily be accommodated by simple microprocessor program code changes thereby substantially eliminating possible instrument obsolescence as improvements in the MIC test panels and biochemical identification panels are made in the future.

Other objects, features, and advantages of this invention will be apparent from a consideration of the following detailed description taken in conjunction with the accompanying drawings.

FIG. 1 is a basic block diagram of a data recording system in accordance with this invention.

FIG. 2 is an isometric view of the cabinet and control panel features of a data recording system in accordance with this invention.

FIG. 3 is an elevational view of a switch panel overlay useful in accordance with one aspect of this invention.

FIG. 4 is an elevational view of a portion of the data entry and control panel features of the instrument depicted in FIG. 2.

FIG. 5 is a block schematic diagram of the electronic data processing circuit portion of a data recording system in accordance with this invention.

FIG. 6 is an exploded isometric view of a multiple copy data form useful in the data recording system in accordance with this invention.

Referring now to FIG. 1, the basic functional blocks of a data recording system in accordance with this invention will be described. As shown in FIG. 1, the simplest version of a data recording system includes a susceptibility test well coordinate entry means 10, a test panel mode data entry means 20, a susceptibility data translation means 40, and a printer 60. The susceptibility coordinate entry means 10 may comprise any data entry means for manually entering susceptibility data in the form of the coordinates of the wells in each set of wells in a test panel at the breakpoint of microorganism growth. This manual data entry is based on visual inspection of the wells of the test panel by a technologist. The test panel mode data entry may comprise any data entry means for entering test mode data corresponding to the test panel type. Printer 60 may be any type of printer capable of printing alphanumeric data on a form. The susceptibility data translation means 40 may be any means for translating the test well coordinate data entered by the coordinate entry means 10 in terms of the entered mode data from mode data entry means 20 into printer drive signals for driving printer 60 to print a list of minimum inhibitory concentrations (MIC's) of the antimicrobics which are utilized in the particular test panel corresponding to the entered test panel mode data.

Susceptibility data translation means 40 includes memory means for storing separate data images of the microorganism type and microorganism concentration for each well coordinate in each particular test panel type. Accordingly, for each of the three currently available test panel types, the gram positive, gram negative, and anaerobic test panels, the susceptibility data translation means 40 stores a data image of the antimicrobics and the test well concentrations for those antimicrobics in accordance with the arrangement for each test panel. The data entered from the test panel mode data entry means 20 into the susceptibility data translation means 40 conditions the data translation means 40 to access the pertinent portions of one of the test panel images stored in memory corresponding to the test panel data entered. The susceptibility test well coordinate data entered via the entry means 10 causes the susceptibility data translation means 40 to read portions of that data image corresponding to the well coordinates entered. The accessed data for each well coordinate is fed to printer 60 to be printed out as part of the MIC listing.

The basic functional blocks of this invention may be implemented using a variety of data entry means and a variety of electronic data translation circuits. A presently preferred system for entering susceptibility test well coordinate data is shown in the instrument in FIG. 2. Here a test well coordinate data entry system incorporates a push button switch array 110 which corresponds generally on a one-for-one basis to the array of wells in the MIC test panel 70. Push button switches are not present on front panel 101 corresponding to the sterility check well 71 or the growth check well 72 on the MIC test panel 70. An additional row of push button switches is provided at the bottom of the array 110 to be utilized to enter a coordinate which signifies that all of the wells in a particular column show organism growth and thus the MIC is greater than that of the highest concentration on the panel.

Accordingly, to enter susceptibility test well coordinate data one of the push buttons in each column corresponding to the breakpoint of microorganism growth is pushed. As will later be described in a more detailed discussion on the instruments depicted in FIG. 2, the pressing of a particular test well coordinate switch causes a corresponding display of a light emitting diode on a circuit board 170 at a test well location corresponding to the switch to register the entry of that test well coordinate. The circuit board 170 with an array of light emitting diodes thereon serves as an entered data display means which enables the technologist to check the accuracy of the test well coordinate data entered. An alternate form of entering test well coordinate data would be to use an array of switches having a mechanical latch which keeps the push button switch down after it is actuated but enables any other push button switch in the column to unlatch a previously actuated switch. Sets of these types of switches could be used for each of the microdilution well series in the test panel 70 with a separate set of switches for the single dilution wells occupying the first row. If the data recording instrument were to be utilized simply to translate well coordinate data into corresponding MIC listings by means of a printer, a fairly simple keyboard multiplexing arrangement together with a hard wired panel memory and a hard wired logic unit for addressing panel images stored in RAM could be utilized to achieve the basic susceptibility data recording of this invention.

There are numerous other ways that susceptibility test well coordinate data entry could be accomplished. For example, a numerical key pad such as key pad 180 could be utilized simply to enter in sequence the appropriate well coordinates for a particular test panel based on assigning each test well a particular coordinate location and marking that coordinate location on the panel. A keyboard interface would store the entered coordinate data and appropriate addressing circuitry would be utilized to access corresponding portions of the test panel data image in an appropriate memory location to obtain the MIC data for printout on the printer.

Another approach that could be taken would be to use separate sets of X and Y coordinate push button switches such that coordinate data for any particular well would be entered into the system by pushing a particular X coordinate switch in coincidence with the actuation of a Y coordinate switch. Another approach that could be used for manual test well coordinate data entry would be to utilize a light-emitting diode array such as the array on circuit board 170 shown in FIG. 2 together with a display driver-scanning arrangement tied into a pair of control switches. The display driver could initially light the LED at one of the test well locations corresponding to a single dilution test well. The technologist would either push a growth or no-growth button with the actuation of the growth button entering a data coordinate for that particular test well and pushing the no-growth button simply causing the display driver to light the LED corresponding to the next test well location. After the single dilution well coordinate data has been entered, the display driver could position the lighted LED at the first test well location in a particular column involving plural dilutions of one of the antimicrobics and the growth (or no-growth switch depending on the scanning direction) could be actuated to step the light-emitting diode to the first test well location showing no growth. Thereupon the pushing of the no-growth switch would cause the entry of that data coordinate and the stepping of the display driver to light the first LED corresponding to the lowest concentration well in the next column. In each column one of the LED's corresponding to the entered no-growth well coordinate would remain lit so that the accuracy of the data entry could be checked after all of the susceptibility test well coordinate data has been entered. It will thus be appreciated that there are a variety of manual data entry schemes which could be utilized in the basic system of this invention, including voice-responsive systems in which the technologist speaks the well coordinate data into a microphone and the spoken data is translated by a speech processor.

Referring back to FIG. 1, a more sophisticated embodiment of this invention incorporates a biochemical test well coordinate entry means 30 together with a biotype data translation means 50 which translates biochemical test well coordinate entries into a corresponding biotype code number. In one version of the invention a generated biotype code number may be simply printed out on a form utilizing data signals sent from biotype data translation means 50 to printer 60. In another version of the invention the biotype data translation means may further include a data memory which stores a data table correlating each of a large number of the biotype identification codes with a corresponding list of probable microorganisms which may produce that particular biotype identification code. The biotype data translation means 50 would then calculate the biotype identification code from the biochemical test well coordinate data entered and utilize the biotype identification code to access memory locations where data corresponding to probable microorganisms is stored. The accessed data signals may then be supplied to the printer 60 for printing the probable microorganism identifications on a form.

The biochemical test well coordinate entry means 30 may utilize any of the coordinate entry approaches which have previously been described. Each of these particular approaches would utilize its own type of keyboard interface. The circuitry to translate the entered coordinate data into corresponding digits of the biotype code could utilize a hard wired logic arrangement to calculate each biotype code digit from the corresponding well coordinate data entered. Various logic system approaches could be taken to provide this function. However, as will be discussed below a preferred embodiment of this invention utilizes a microprocessor-based arrangement to serve both as susceptibility data translation means 40 and biotype data translation means 50 with appropriate software program coding instructing the microprocessor to perform each of these functions in conjunction with read-only memory and random access memory units which store susceptibility test panel data images and entered test well coordinate data.

Referring now to FIGS. 2-6, a preferred embodiment of a data recording system in accordance with this invention will be described. As shown in FIG. 2, the preferred embodiment comprises a data recording instrument 100 which is housed in an instrument cabinet 105. The front panel 101 of cabinet 105 has mounted thereto an array 110 of susceptibility well coordinate switches, an array 130 of biochemical test well coordinate switches, a switch column 120 for test panel mode data entry, a numeric key pad 180 for entering patient identification information and various epidemiology data under the control of a column of epidemiology data function entry switches 190.

A test panel well 102 is located in a front panel 101 for receiving one or both of a MIC test panel 70 and a biochemical ID panel 80. A test panel switch overlay 90 may be provided for mounting over the susceptibility test switch array 110 and the biochemical test switch array 130. The detail of the descriptive legends on a gram negative MIC/ID overlay are shown in FIG. 3.

In the bottom of the test panel receiving well 102 is a circuit board 170 having a matrix of individual LED's 171 mounted thereon. In addition, the circuit board 170 has an array of apertures 172 formed therein for admitting light into the MIC and ID test panel wells. Behind the test panel 101 adjacent the test panel well 102 is a lighting arrangement (not shown) for illuminating the MIC and ID test panels mounted within the test panel well.

In addition to the LED array mounted on circuit board 170, a column of LED's 175 is provided adjacent the biochemical data entry switch array 130 for signaling the entry of secondary and off-panel test data coordinates for the right-hand column of switches in the array 130. Each of the mode switches in column 120 has a corresponding LED 176 associated with it. Similarly, each of the epidemiology function switches in column 190 has an LED 177 associated with it. An eight-digit LED display 200 is provided for displaying the biotype code number as it is generated and displaying certain of the data entered under control of the function switches in column 190, such as the patient identification number, age, hospital site, and organism code and data entry error codes. The electrical circuit interconnection of all of the switch arrays, and LED display arrays will be discussed below in conjunction with the electronic data processing system block diagram depicted in FIG. 5.

In the top right-hand portion of the instrument cabinet 105 is a printer housing 160 wherein is mounted an alphanumeric printing mechanism. A multi-copy form 210, the details of which will be described later, may be inserted into the printer mechanism within housing section 160 via a slot 162. The form 210 is guided into the print mechanism by an adjustable side guide arrangement 161 in order to maintain precise registration of the form with respect to the print head in the unit. This alignment is required for accurately printing a machine-readable code in a registered location on the form 210. The overall functioning of the instrument 100 will be described below in terms of a specific example of a data recording sequence. FIG. 3 illustrates the gram negative MIC/ID switch array overlay with the information that is printed thereon. The dashed and dotted lines shown on FIG. 3 represent the biotype code number scheme previously described and are not actually printed on the overlay itself. FIG. 4 illustrates in greater detail the mode switch array 120, the seven-segment LED display 200 and the function switch array 190 whose operation will be described in conjunction with a specific example given below.

Referring now to FIG. 5, the microprocessor-based data processing system and control used in a preferred embodiment of this invention will be described. A microprocessor chip arrangement 220 is utilized which includes a clock and control chip 221, a microprocessor chip 222, and a two-way data buffer and control signal circuit 223. The microprocessor chip set 220 comprises a standard Intel 8080 type of chip set. Other microprocessor types such as the Zilog Z 80 microprocessor could also be employed in the microprocessor arrangement 220 but the overall function and performance would be essentially the same. Microprocessor arrangement 220 includes an address bus 224, a two-way data bus 225, and a control signal bus 226. Each of these buses communicate with various of the memory and data and ports which are provided in the system. Program and data read-only memory (ROM) 240 is coupled to the address bus 224 and to the data bus 225. A scratch pad random access memory (RAM) 250 is coupled to address bus 224, two-way data bus 225, and control signal bus 226. Two programmable input/output (I/O) ports 260 and 300 are also coupled to each of these buses as are two input ports 350 and 360. The programmable I/O port set 260 is dedicated to providing control and data signals to a printer driver 270 for controlling the operation of a print mechanism 280. Two of the eight-bit ports on the programmable I/O 260 are utilized to communicate data and control signals to printer driver 270 and a third port receives signals fed back from printer driver 270 to form a closed loop control system which enables the microprocessor to keep track of the print head position.

The programmable I/O ports 300 are devoted to data and control signal communication between the microprocessor arrangement 220 and a keyboard interface 310 and a plurality of display processors 330. The keyboard interface 310 communicates with a key switch matrix 320 which includes all of the switch arrays 110, 130, 120, 180, and 190 on the front panel 101 shown in FIG. 2. It also includes a top of form sense arrangement 290 which is physically located in the printer area. These switch arrays are connected into an X-Y matrix which is interrogated under microprocessor program control via the keyboard interface 310 to detect key switch actuation and to communicate to the microprocessor 220 data indicating the X-Y coordinate of the actuated switch. The two output ports of programmable I/O 300 are also coupled to a plurality of display processors 330 which control the lighting of the LED displays 340, including all of the LED arrays on the front panel 101 shown in FIG. 2 together with the seven-segment display 200. In the instrument four LED processor chips of the type available from Intersil as Part Number ICM 7218AIJI are utilized. Two of the LED processor chips control the lighting of LED's in the matrix array on circuit board 170 in the test panel well 102. One of the LED processor chips controls the information displayed on the seven-segment multi-digit display 200 on the front panel. The fourth LED processor chip controls the LED array 175 and the LED's 176 and 177 associated with the column of switches 120 and 190. These display processors include data buffers which hold display coordinate information downloaded from the microprocessor through the programmable I/O 300 and provide corresponding display driver signals to the LED displays 340 to maintain the LED light pattern without refresh signals from the microprocessor.

The two input ports 350 and 360 connected to switches 370 and 375 are utilized for communicating a Microdata Services account number which is set into the switches 370 and 375 to the microprocessor so that that number can be placed in the machine-readable code which is printed on the form 210 under microprocessor program control.

In addition to the two programmable I/O's 260 and 300, the system may include additional I/O devices for communicating in an on-line fashion with other systems. For example, the microprocessor-based processing and control system depicted in FIG. 5 could be interfaced via a programmable I/O port to a general purpose computer programmed to accumulate and process antibiogram data from a plurality of individual MIC and identification tests performed utilizing the instrument of this invention. The system depicted in FIG. 5 could further be configured to have an I/O port dedicated to remote data communication by way of a modem.

The program and data ROM 240 contains operating program instruction for the microprocessor 220 and also stores data images corresponding to the antimicrobics in single and serial dilutions for each of the gram negative, gram positive, and anaerobe MIC test panels which are currently available. A urine panel will eventually be available and the program and data ROM which is either EPROM or EEPROM type memory can be easily modified to handle the new panel. In addition, program and data ROM 240 stores a data lookup table containing microorganism names and probability statistics for each of a large number of biotype code numbers. Program and data ROM 240 also contains the necessary microprocessor operating instructions and character generation data to be communicated through programmable I/O 260 to printer driver 270.

Referring to FIG. 5 in conjunction with FIG. 2, the overall general operating program of the system will be described. Basically the microprocessor operating program stored in program and data ROM 240 establishes a first microprocessor operating status during which the programmable I/O 300 is active, the microprocessor is interrogating the keyswitch matrix array 320 to look for keyswitch actuations and is processing those key switch actuations into appropriate stored data in scratch pad RAM 250, some of which data is also downloaded into the display processors 330 to control the lighting of the various LED's in arrays and seven-segment displays. The microprocessor exits this operating status when a top of form sense signal is received from top of form sense circuit 290 through the keyswitch matrix 320 and the microprocessor enters a second operating status during which a sequence of data communication and data processing steps are carried out. There are a number of possible approaches to sequencing these data processing steps but the end result is to print out, in a predefined format, both human-readable data and a machine-readable code on the form 210 depicted in FIG. 6. A particular exemplary sequence of these data processing and communication steps will be generally discussed in connection with a specific example of the operation of the system given below.

Referring now to FIG. 6, a preferred embodiment of a form to be utilized in the data recording instrument of this invention will be described. As shown, the form 210 comprises three separate data recording sheets 211, 213, and 216. A carbon sheet 212 is provided between the top sheet 211 and the intermediate sheet 213 and a second carbon sheet 215 is provided between the intermediate sheet 213 and the bottom sheet 216. The intermediate sheet 213 comprises a self-adhesive peel off sheet which is carried on a release sheet 214.

The three form sheets 211, 213, and 216 are bound together at the top portions 211A, 213A, and 216A with adhesive. Each of the sheets is perforated at the top for separation as, for example, at the perforation line 211B shown on the form 211. The top form 211 is designed as an optical character reader input form and includes a machine-readable code section 211F at the bottom of the form. Above the machine-readable code section 211F are three human-readable data sections shown within dashed rectangles generally designated 211C, 211D, and 211E.

The intermediate sheet 213 is designed as a peel off label sheet and has two separate sections 213B and 213C with a perforation 213D enabling the two sections to be separated and used as labels to be placed in a log book and on a patient report form. The bottom sheet 216 is a heavy weight carrier card which also has all of the human-readable and machine-readable information printed thereon.

In Table 1 below an example of a printout on the form 210 is shown. The mark sense machine-readable code is shown as an array of asterisks but would actually be a solid rectangle in the printout. The manner in which the instruments shown in FIGS. 2–5 was operated to produce this printout will now be described. As shown on the sample printout in Table 1 in the second print line the test panel type is a gram negative MIC/ID panel. t,0290
Accordingly, in producing this printout the technologist would have set up a gram negative MIC panel and a gram negative ID panel in accordance with the procedure previously described and incubated the panel for the prescribed period of time. Referring to FIG. 2, the MIC panel 70 and the ID panel 80 would then be placed in the reading well 102 for reading the wells in both panels. If the instrument has previously been used to record information from a previous panel, the reset switch shown in FIG. 3 would be pushed to clear all data from the instrument. At this point the microprocessor control and processing system depicted in FIG. 5 is in its first operating status and is interrogating the various switches on front panel 101 to detect switch closures.

The system does not require that the technologist enter information in any particular order, but an order will be assumed for purposes of this discussion. Since the MIC panel is a gram negative panel, corresponding test panel mode data is entered by pressing the gram negative switch in the column 120 shown in FIG. 4. When this switch is actuated the microprocessor detects the switch closure, determines the coordinate of the switch, stores the corresponding data coordinate in scratch pad RAM 250, and downloads appropriate coordinate data into the display processors 330 to light the LED in the top left-hand corner of the gram negative switch area. This all happens within a matter of microseconds and the technologist immediately sees the lighted LED, indicating that the test panel mode entry has been received by the system. At this point the technologist begins to enter the susceptibility data from the MIC test panel. The technologist looks at the first column of test wells and determines that the lowest concentration well in which no microorganism growth is observed is in row four of the first column of wells. Consequently, the technologist pushes the third from the top switch in column one of switch array 110. The microprocessor recognizes the switch closure, determines the coordinates of the switch, enters the coordinate data into the scratch pad RAM 250 and downloads it into the display processors 330 to light corresponding LED at the corresponding test well location on circuit board 170.

If the technologist changes his mind as to the location of the no-growth well or realizes that he has pushed the wrong switch in the first column because the LED lights in a different place than he anticipated, the technologist can simply push another switch in that column to change the entered well coordinate data. The microprocessor will recognize the second switch closure as being in the same column, and will erase the data entered from the first switch closure and process the data from the second switch closure as previously described. If the technologist wishes to record a no-entry for any particular antimicrobic, but has already entered a particular well coordinate by pushing one of the switches, he can erase the coordinate entry by pushing the same switch again. The microprocessor recognizes the second switch closure as an erase signal for that data coordinate entry and erases the well coordinate data stored in the scratch pad RAM 250 and unloads it from the display processors 330.

The technologist would proceed to read the other nine columns in the MIC test panel, each time entering the susceptibility test well coordinate by pushing an associated push button switch. In the second column the seventh switch from the top is actuated corresponding to the last well in that column of the panel. This corresponds to no-growth in the last well in the second column of the test panel 70. The technologist would continue to read each column of the panel each time entering the coordinates of the well showing no-growth by pushing the corresponding push button switch in the appropriate column of the switch array 110. The switches which are actuated as the technologist reads the multidilution antimicrobic columns are marked with an X in FIG. 3. In the fourth column the technologist has actuated the last switch indicating that the microorganism is growing in each of the Tetracycline test wells in that column on panel 70. This means that the minimum inhibitory concentration of that particular antimicrobic is greater than any concentration, if any, on the panel. In the sixth column the technologist has pushed the switch corresponding to the first test well containing Chloramphenicol. This indicates that the technologist sees no growth in any of the test wells containing Chloramphenicol. The remainder of the test well coordinate entries are as shown marked with an X in FIG. 3.

Next the technologist reads the single dilution wells and actuates the first switch in row one indicating no growth in Colistin, leaves unactuated the second switch in that row, indicating growth in Nitrofurantoin, pushes the third switch indicating no growth in Trimeth/Sulfa, and pushes the fourth switch indicating no growth in Kanamycin. The remainder of the switches in the first row have no function and will be ignored.

At this point if the technnologist were not also doing an ID panel data entry he would continue on by entering the appropriate epidemiology data using the switch panel 190 and keypad 180 illustrated in FIG. 4. However, in this case a gram negative ID panel is also being employed and the data entry from that will be described. In setting up the ID panel, the technologist will have already performed an Oxidase test and determined that the microorganism is Oxidase negative. From this and other information the technologist will anticipate an enteric organism and this will be confirmed by the positive test result in the Dextrose (Dx) well of the biochemical panel 80. Since Oxidase was negative, the Oxidase switch which is the top switch in the fourth column of the switch array 130 will not be pushed. However, the technologist notes positive reactions in Dextrose and VP and accordingly pushes the Dx and VP switches which are the top two switches in column 1 of the array 130.

As the Dx switch is pushed, the microprocessor recognizes the switch closure, determines the coordinate of that switch closure, recognizes it as a biochemical test well data entry, and performs a calculation and storage subroutine which assigns the point value number "2" to that switch closure for the first digit of the biotype code. This point value number two is stored in the scratch pad RAM 250 at an appropriate location and is downloaded to the display processors 330. One of the display processors lights the corresponding LED under that test well location on circuit board 170, and another of the display processors causing the digit "2" to be displayed as the left-most digit on the seven-segment display 200. When the second switch in the first column of the switch array 130 is then actuated, the microprocessor detects that switch coordinate and performs the same calculation and storage subroutine assigning the point value "1" to that switch closure, adding that point value to the previously stored point value "2", and storing the resultant point value "3" in an appropriate storage location in scratch pad RAM 250. Both the switch coordinate location data and the point value "3" data are then downloaded to the display processors 330 through programmable I/O 300 to cause a lighting of the corresponding LED adjacent the VP test panel well and to cause the digit three to be displayed in the left-most digit on the seven-segment display 200.

The technologist reads in sequence the next three wells in the first column and notes a positive reaction in the ONPG well (ON) and pushes the corresponding switch in switch array 130. The microprocessor responds in similar fashion to this switch closure and lights the corresponding LED adjacent the test well and causes the digit "4" to be displayed in the second digit location of display 200. The Hydrogen Sulfide (H$_2$S) and Lysine (Ly) wells show negative so neither the corresponding switches are pushed. Accordingly, the second digit of the biotype code becomes a "4" which is stored in the scratch pad memory 250 and displayed on the seven-segment display 200.

The next three wells in the first column are read. The Arginine (Ag) and Ornithine (Or) show a negative and the Urea (Ur) show a positive. Consequently, only the corresponding Ur push button switch is actuated by the technologist, causing the microprocessor to develop the digit "1" to be stored in memory and displayed on the LED seven-segment display 200 in the third digit location. For the fourth digit, the technologist knows that he is dealing with an enteric organism and the test wells corresponding to the fourth digit are the Citrate (Ci), Malonate (Ma), and Tryptophane Deaminase (TDA). (If it had been a non-enteric organism, the Indole reaction data would be entered into the system at this point.) Since both the Citrate and Malonate tests are positive, the technologist pushes both the corresponding coordinate switches in the array 130. The microprocessor responds to these two switch closures to develop the code digit "6" in the manner similarly described and this digit is stored in the scratch pad RAM 250 and downloaded to the display processors 330 as previously indicated.

The technologist continues reading the appropriate test reactions for the enteric organisms and entering the corresponding positive reactions by pushing switches corresponding to the test well locations showing a positive reaction. On FIG. 3 the switch locations which are entered to develop the biotype code "3416377" shown in Table I are marked with an asterisk. After all of the biotype data has been entered the technologist can use the lighted LED pattern under the biochemical test well to check the positive reactions entered and, if desired, can verify by manual calculation the biotype code number generated in accordance with the entered reaction data.

Having entered the susceptibility data coordinates and the biochemical data coordinates, the technologist then can complete his data entry by putting in the patient identification and epidemiology data using the switch column 190. Actuation of the Patient Ident. # switch is recognized by the microprocessor and conditions it to respond to the entries on the key pad 180 to treat them as patient identification data and to enter that data in an appropriate designated location in scratch pad RAM 250. Actuation of the Age switch is detected by the computer which is then conditioned to treat the next segment of entered data on the key pad 180 as age data for storage in an appropriate location in scratch pad RAM 250. Similarly, sex, body site, and hospital site data can be entered in sequence. The sex information utilizes the keys corresponding to the number "7" or "8" on the key pad 180 and the body site data is entered utilizing the legends depicted on the bottom of each of the key pads "0" through "9" given as URINE, WOUND, RESP (respiratory), ABCES (abscess), BLOOD, CSF (cerebral spinal fluid), GENIT (genital), STOOL, B.FLDS (body fluids), OTHER. The enter and clear buttons are utilized to signal the microprocessor to enter the particular key pad data and to clear the key pad data for correction and re-entry as necessary. The Hospital Site switch may be pressed to enter a code number corresponding to the location in the hospital in which the microorganism originated. The Organism Code switch enables the technologist to enter his own identification of the organism which overrides any biotype code entered in accordance with identification well coordinate data.

In addition to the test panel mode data which may be entered using the switches in column 120 the Beta Lactamase (BetaLact) or the Calcium Magnesium (Ca/Mg) switches may be actuated by the technologist under appropriate conditions either to indicate that the organism is Beta Lactamase positive. This button may be pushed for gram positive microorganisms to cause a printout on the form that the organism is Beta Lactamase positive and thus inform the physician that penicillin and ampicillin should not be utilized for patient treatment. To reemphasize this, the technologist may avoid any data entry for the penicillin and ampicillin columns in the gram positive MIC panel which will cause a no-entry printout on the form. The Ca/Mg switch may be pushed if Calcium/Magnesium supplement is added to the wells. This will cause a printout of Calcium/Magnesium as a well constituent on the printed form. The use of Calcium/Magnesium supplement will make the organisms look more resistant to the antimicrobics, so printing this on the form permits the physician to take this into consideration in determining the concentration of antimicrobic to use in treating the patient.

At this point all of the test panel, test mode, and epidemiology data has been entered and the technologist is ready to have a printout of the entered data. The printout is initiated by inserting a form in the printer slot 162 shown in FIG. 2. A Top of Form Sense mechanism within the printer (which may be a LED/LRD combination) senses the form entry and sends a signal through the keyswitch matrix 320 (FIG. 5) to the microprocessor. This causes the microprocessor to enter a second operating status and to automatically go through a series of program steps stored in program and data ROM 240. Basically at this point, microprocessor 220 will access under program control portions of the information stored in scratch pad RAM 250 in sequence and utilize that information either to provide data and control signals directly to the printer driver and control 270 through programmable I/O 260 or to utilize that information to look up data in program and data ROM 240 to be sent to the printer driver and control 270 through I/O ports 260.

Operating under program instruction control from program and data ROM 240, the microprocessor will first retrieve the patient identification number from scratch pad RAM 250 and communicate corresponding drive signals to the printer driver and control 270 to cause a duplicate printout of the patient identification number on the right and left halves of the form in the area designated 211C in FIG. 6. Next the microprocessor will access the test panel mode data in scratch pad RAM 250 and cause it to be printed out as the second line, again in duplicate on the right and left halves of the form 210 in the area 211C. The next two lines on the form are reserved for a printout of an indication of Beta Lactamase positive and Calcium/Magnesium used, but no such data entries have been made for this particular test. Consequently, these lines of the form are blank.

Next the microprocessor will begin processing the susceptibility data to develop MIC information for printout on the form. A standard heading as shown in Table I is first printed and then the microprocessor utilizes the entered susceptibility data well coordinates stored in scratch pad RAM 250 together with the test mode data to access pertinent portions of a data image stored in program and data ROM 240 corresponding to the gram negative MIC panel. Each entered multidilution well coordinate data item will be retrieved in sequence and a corresponding drug name identification, antimicrobic concentration of the well, and level of susceptibility will be printed out as shown in Table I.

After all of the MIC information has been printed out, the microprocessor responds to program instruction to retrieve the biotype code number and send data to the printer to print it out as the next line on the form. Thereafter the microprocessor utilizes the biotype code number to look up corresponding probable microorganism identifications in a large look up table stored in program and data ROM 240 and sends the appropriately retrieved data to the printer driver and control for printout on the form.

After printing out the probable microorganism identifications, the microprocessor begins to execute a couplet separation subroutine which utilizes the organism code identification together with portions of the MIC information to calculate the most probable microorganism and to print out an identification of the most probable microorganism to a level of confidence of at least ninety percent. The implementation of this subroutine uses couplet separation data which is proprietary to Micro-Media Systems, Inc., and does not constitute a portion of this invention except to the extent that the overall microprocessor-based features of this invention enable the implementation of the couplet separation technique as a software program component of the instrument.

Following this couplet separation printout of the most probable microorganism, the microprocessor sends data and control signals to the printer driver and control circuit 270 to print out a machine-readable code format which contains the Micro-Media customer identification number, the MIC information, the biotype code information, and the epidemiology data. All of this data can be encoded in various ways and the details of that coding is not pertinent to this invention. The purpose of the machine-readable encoding on the form is to permit an optical character reader to read the data and enter it into a data base for further data accumulation, processing and reporting.

After the form has been completely printed, the printer mechanism kicks the form back out of the printer and the technician can then separate the various print form copies. The top copy of the form is accumulated with others to be sent to the Micro-Media data services bureau for entry of the information into a data bank. The two peel off labels may be separated from the intermediate sheet 213 in FIG. 6 and placed on the appropriate log book location and patient report form location. The card copy of the printout may be utilized for whatever purposes the hospital wishes to utilize this extra printout. If additional peel off labels are required, a second form can be entered and printed out in the same fashion without having to reenter data.

The printout processing program executed by the microprocessor is different for the other two types of MIC panels in that no biochemical data has been entered for those panels. Accordingly, the computer will skip this portion of the program steps and, after printing out the MIC information, the computer will immediately proceed to print the machine-readable code format on the bottom of the form.

Although the data recording apparatus and method of this invention have been described above in conjunction with a preferred embodiment and certain alternative embodiments, it should be understood that numerous modifications could be made without departing from the scope of the invention as claimed. In particular, it should be understood that the invention encompasses a number of ways of manually entering susceptibility well coordinate data and biochemical test well coordinate data. In addition the invention encompasses various hard wired logic systems for processing the entered information in addition to the programmed microprocessor-based system which has been described above. With respect to the specifics of well coordinate data entry described in connection with the preferred embodiment of the instrument, it should be understood that the breakpoints in microorganism growth could be entered as either the last well to show growth or the first well not to show growth, with the microprocessor programmed to respond accordingly to print out appropriate MIC values. Similarly, the well coordinate data entry for the biochemical tests could utilize the entry of negative reaction instead of positive reactions, with the microprocessor programmed to react accordingly in generating the biotype code digits. Numerous other modifications could be made without departing from the scope of this invention as claimed in the following claims.

What is claimed is:

1. In a system for recording susceptibility data from one of a plurality of microdilution test panel types corresponding to a predetermined one of a plurality of types of microorganisms and having at least a plurality of sets of wells each having a series of prearranged different dilutions of preselected different antimicrobics, which wells have been innoculated with prearranged amounts of an unknown microorganism and incubated to promote microorganism growth, in combination:
   first data entry means for manually entering susceptibility data in the form of the coordinates of one of the wells in each of said sets at the breakpoint of microorganism growth based on visual inspection of said wells of said test panel;
   second data entry means for entering test mode data corresponding to said test panel type;
   a printer for printing alphanumeric data on a form; and
   susceptibility data translation means for translating said entered susceptibility data in terms of said entered mode data into printer drive signals for driving said printer to print on said form a listing of minimum inhibitory concentrations of said antimicrobics for said unknown microorganism.

2. Apparatus as claimed in claim 1, further adapted for recording biotype data from a biochemical microorganism identification panel having an array of test wells containing different biochemical media which have been innoculated with an unknown microorganism and from a plurality of separate tests secondarily conducted on said identification panel or conducted off said panel, and further comprising:
   third data entry means for manually entering biotype data in the form of the coordinates of wells having a prearranged one of a predefined positive or negative reaction and the preassigned coordinates of said secondary and separate tests having a prearranged one of a predefined positive or negative reaction; and
   biotype data translation means for translating said entered biotype data into printer drive signals for driving said printer to print out at least one probable microorganism identification corresponding to said entered biotype data.

3. Apparatus as claimed in claim 2, further comprising:
   first data display means including an array of visual display elements corresponding substantially to the geometric arrangement of said sets of wells in said microdilution test panel;
   second data display means including an array of visual display elements corresponding substantially to the geometric arrangement of said wells in said biochemical identification panel;
   third data display means including a plurality of visual display locations assigned to said secondary panel and off panel biochemical tests; and
   display driver means for translating said entered susceptibility data and said entered biochemical test data into display driver signals for causing said first display means to display visual indicia of entered susceptibility well coordinates, for causing said second display means to display visual indicia of entered on-panel biochemical test well coordinates, and for causing said third display means to display visual indicia of entered coordinates of said secondary and off panel tests.

4. Apparatus as claimed in claim 3, wherein said data recording system is housed in an instrument cabinet having a front panel and said front panel includes a well adapted to receive a microdilution test panel and a biochemical identification panel in side-by-side relation, and panel illuminating means are mounted under said front panel for illuminating both said test panel and said identification panel;
   said first data entry means comprises a plurality of sets of switches mounted to said front panel in a location adjacent said panel receiving well, said sets of switches being arranged in a geometric array corresponding substantially to the geometric arrangement of said sets of wells in said microdilution test panel for manual entry of said susceptibility coordinate data by actuation of one of said switches corresponding to an associated well location in said test panel;
   said third data entry means comprises a plurality of sets of switches mounted to said front panel in a location adjacent said panel receiving well, a first portion of said sets of switches being arranged in a geometric array corresponding substantially to the geometric arrangement of said sets of wells in said biochemical identification panel and one set of said switches being arranged adjacent said array of first sets to serve as data entry means for said secondary and off panel tests; and
   said data display means comprises a circuit board mounted in said panel receiving well having a first plurality of lights mounted thereon in an array corresponding to the array of wells in said test panel at positions located adjacent corresponding well locations in a microdilution test panel located in said well and a second plurality of lights mounted thereon in an array corresponding to the array of wells in said biochemical identification panel at locations adjacent corresponding well locations in an identification panel located in said well, and a set of lights mounted in said front panel adjacent said second set of switches designated for entry of data corresponding to said secondary and off panel biochemical tests.

5. Apparatus as claimed in claim 4, wherein said switches in each array are push button switches, and further comprising a plurality of switch overlays each corresponding to an associated one of said test panel types and adapted to be placed over said switch arrays, each of said switch overlays having printed thereon antimicrobic names associated with each set of switches and concentration values at locations corresponding to each well location associated with each push button switch; at least some of said overlays having printed thereon identification of the biochemical test corresponding to well locations in said biochemical identification panel.

6. Apparatus as claimed in claim 2, wherein said first data entry means comprises a first plurality of sets of switches arranged in a geometric array corresponding substantially to the geometric arrangement of said sets of wells in said microdilution test panel for manual entry of said susceptibility coordinate data by actuation of one of said switches corresponding to an associated well location; and said third data entry means comprises a second plurality of sets of switches arranged in a geometric array corresponding substantially to said array of biochemical test wells together with a separate set of switches for said secondary and off panel tests, said sets of switches being adapted for manual entry of said biochemical test data by actuation of one of said switches corresponding to an associated biochemical test panel well location or to an assigned coordinate location for a secondary or off panel test.

7. Apparatus as claimed in claim 2, wherein said susceptibility data translation means produces printer drive signals for driving said printer to print a human-readable listing of minimum inhibitory concentrations of said antimicrobics on one portion of a form; said biotype data translation means produces printer drive signals for driving said printer to print out a human readable biotype identification code word on a second portion of said form and both said susceptability data translation means and said biotype data translation means produce printer drive signals for driving said printer to print a machine-readable code format of said minimum inhibitory concentration of said antimicrobics and of said biotype identification code on a third portion of said form.

8. Apparatus as claimed in claim 1, further comprising susceptibility data display means including an array of visual display elements corresponding substantially to the geometric arrangement of said sets of wells in said microdilution test panel; and display driver means for translating said susceptibility data into display driver signals for causing said display means to display visual indicia of entered well coordinate data.

9. Apparatus as claimed in claim 8, wherein said data recording system is housed in an instrument cabinet having a front panel, said front panel includes a test panel well adapted to receive said test panel and illumination means mounted under said front panel for illuminating said test panel;

said first data entry means comprises a plurality of sets of switches mounted to said front panel in a location adjacent said panel receiving well, said sets of switches being arranged in a geometric array corresponding substantially to the geometric arrangement of said sets of wells in said microdilution test panel for manual entry of said susceptibility coordinate data by actuation of one of said switches corresponding to an associated well location in said test panel; and said data display menas comprises a circuit board mounted in said test panel well and having a plurality of lights mounted thereon in an array corresponding to the array of wells in said test panel at the positions adjacent corresponding well locations in a test panel received in said well.

10. Apparatus as claimed in claim 1, wherein said first data entry means comprises a plurality of sets of switches arranged in a geometric array corresponding substantially to the geometric arrangement of said sets of wells in said microdilution test panel for manual entry of said susceptibility coordinate data by actuation of one of said switches corresponding to an associated well location.

11. Apparatus as claimed in claim 1, wherein said susceptibility data translation means produces printer drive signals for driving said printer to print a human-readable listing of minimum inhibitory concentrations of said antiomicrobics on one portion of said form and to print a machine-readable code format of said minimum inhibitory concentrations on a second portion of said form.

12. Apparatus as claimed in any of claims 11 or 7, further comprising manual data entry means for entering patient identification data and epidemiological data related to the microorganism sample being tested; and data translation means for translating said patient identification data into printer drive signals to drive said printer to print said patient identification data in human-readable form on a prearranged portion of said form and to drive said printer to print said eipdemiological data in machine-readable code format in a prescribed location on said machine code portion of said form.

13. Apparatus as claimed in claim 1, wherein said printer comprises a printer mechanism and a printer drive circuit adapted to respond to input data and control signals to print alphanumeric characters on a predesigned form and said antibiogram data translation means comprises:

a microprocessor having address, data, and control signal buses;

a first programmable port coupled to said address, data, and control buses for selectively supplying data and control signals to said printer drive circuit under microprocessor program control;

a second programmable port coupled to said first and second manual data entry means and to said address, data, and control buses for enabling said microprocessor to receive said susceptibility data and said test mode data;

a random access memory coupled to said address, data, and control signal buses for storing said antibiogram data and test mode data under microprocessor program control;

a program and data memory coupled to said address and data buses for storing microprocessor operating program codes and a plurality of minimum inhibitory concentration data images each corresponding to all susceptibility data coordinates for a particular microdilution test panel type;

said microprocessor operating program codes establishing a first microprocessor operating status during which said second programmable port is active to permit entry and storage of said susceptibility and test mode data and a second microprocessor operating status during which said second programmable port is active and said microprocessor is operated to utilize said stored susceptibility and test mode data to selectively access portions of a corresponding minimum inhibitory concentration data image in said program and data memory for communicating corresponding data and control signals to said printer through said second programmable port thereby causing said printer to print said listing of minimum inhibitory concentrations of said antimicrobics for said unknown microorganism.

14. Apparatus as claimed in claim 13, wherein said first data entry means comprises a plurality of sets of momentary contact switches arranged in a geometric array corresponding substantially to the geometric arrangement of said sets of wells in said microdilution test panel for manual entry of said susceptibility coordinate data by actuation of one of said switches corresponding to an associated well location; said apparatus further including a first data display means including a plurality of display elements arranged in an array corresponding substantially to the geometric arrangement of said sets of wells in said microdilution test panel; and display driver means coupled to said second programmable port for driving said display means to actuate display elements corresponding to entered susceptibility well coordinate data under microprocessor control.

15. Apparatus as claimed in claim 14, wherein said display driver means includes data storage means for storing display element coordinate data downloaded from said microprocessor and said microprocessor program operating codes stored in said program and data memory program said microprocessor to respond to a first closure of any of said momentary contact switches to store a corresponding susceptibility well coordinate in said random access memory and to download a corresponding well coordinate signal to said display driver means; said codes further programming said microprocessor to respond to a second closure of any of said momentary contact switches to erase said susceptibility well coordinate data from said random access memory and to unload said well coordinate data from said display driver means.

16. Apparatus as claimed in claim 13, further comprising a third data entry means coupled to said second programmable port for manually entering biotype data in the form of the coordinates of wells in a biochemical identification panel having a prearranged one of a positive or negative reaction; and said microprocessor program codes active during said first microprocessor operating state include microprocessor program instructions for translating each of said entered biotype data coordinates into an associated biotype code digit value, for summing said biotype code digit values with others previously entered and for storing said summed biotype code digit value in said random access memory; and said microprocessor program codes active during said second microprocessor operating state include microprocessor program instructions for retrieving said stored biotype code digit values and for communicating corresponding data signals to said printer for printing a biotype identification code number on said form.

17. Apparatus as claimed in claim 16, wherein said program and data memory also stores a data table which correlates each of a large number of said biotype identification codes with a corresponding list of probable microorganisms which may produce such biotype identification code, and said microprocessor program codes which are active during said second operating state include microprocessor program instructions for looking up said probable microorganism data based on said stored biotype identification code and for communicating corresponding data signals to said printer for printing out said probable microorganism identifications on said form.

18. Apparatus as claimed in claim 16, wherein said microprocessor program codes active during said second operating state of said microprocessor include microprocessor program codes for supplying data and control signals to said printer for printing on one section of said form human-readable listings of said minimum inhibitory concentration data, said biotype code and said probable microorganism identifications and for printing on a second section of said form a machine-readable code format of said minimum inhibitory concentration data and said biotype code.

19. Apparatus as claimed in claim 1, wherein said form is a multi-sheet, duplicating data form having at least one sheet with at least a pair of peel off self-adhesive labels thereon, and said susceptibility data translation means drives said printer to print a duplicate of said minimum inhibitory concentration listing on each of said peel off labels.

20. A method for processing manually-entered antibiogram data from one of a plurality of multidilution test panel types designed for a predetermined one of a plurality of types of microorganisms and having at least a plurality of sets of wells each having a series of prearranged different dilutions of preselected different antimicrobics, which wells have been innoculated with prearranged amounts of an unknown microorganism and incubated to promote microorganism growth, the method comprising:
  storing in read-accessible memory a separate data image of the antimicrobic concentrations for all of said wells in each of said test panel types in terms of the associated well coordinates;
  conditioning data addressing of said read-accessible memory to one of said data images based on entered test panel-type data;
  reading antimicrobic concentration values from said one data image in said read-accessible memory based on manually entered well coordinate data determined from visual inspection of said test panel wells; and
  printing a listing of said read antimicrobic concentration values on a prescribed form as the minimum inhibitory concentrations of said antimicrobics for said unknown microorganism.

* * * * *